(12) United States Patent
Roberts et al.

(10) Patent No.: US 6,585,953 B2
(45) Date of Patent: Jul. 1, 2003

(54) SYNTHESIS OF 17F LABELED FLUOROALKANES

(75) Inventors: Andrew D. Roberts, Madison, WI (US); Robert J. Nickles, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 09/845,639

(22) Filed: Apr. 30, 2001

(65) Prior Publication Data

US 2002/0028177 A1 Mar. 7, 2002

Related U.S. Application Data

(60) Provisional application No. 60/230,780, filed on Sep. 7, 2000.

(51) Int. Cl.[7] .............................................. A61K 51/00
(52) U.S. Cl. ..................................................... 424/1.89
(58) Field of Search ........................ 424/1.89; 570/123, 570/124, 134, 135, 136, 153, 156, 159, 176

(56) References Cited

U.S. PATENT DOCUMENTS

4,523,040 A  *  6/1985  Olah ........................... 568/671

OTHER PUBLICATIONS

Dabbs, Kevin A., Individual National Research Service Award Application, signed Nov. 12, 1999.
Eichling, John O., et al., "Evidence of the Limitations of Water as a Freely Diffusible Tracer in Brain of the Rhesus Moneky," 35, Circ. Res., 358–364 (1974); Lippincott, Williams & Wilkins, Baltimore.
Gatley, S. J., et al., "18F–labeled Lower Fluoroalkanes; Reactor–produced Gaseous Physiological Tracers," 32, Int. J. Appl. Radiat. Isot., 211–214 (1981); Elsevier, New York.
Gatley, S. J., et al., "An Improved Synthesis of the Inert, Diffusible Blood–flow Tracer, [18F] Fluoromethane," 42, Appl. Radiat. Isot., 1049–1053 (1991); Elsevier, New York.
Herscovitch, P., et al., "Positron Emission Tommographic Measurement of Cerebral Blood Flow and Permeability—Surface Area Product of Water Using [15O]Water and [11C]Butanol," 7, J. Cereb. Blood Flow Metab., 527–542 (1987); Raven Press, Ltd., New York.
Martin, C. C., et al., "Effect of Partition Coefficient, Permeability Surface Product, and Radioisotope on the Signal–to–Noise Ratio in PET Functional Brain Mapping: A Computer Simulation," 7, Human Brain Mapping, 151–160 (1999); John Wiley, New York.
Mulholland, G. K., et al., "Posterboard 899," 28, J. Nuc. Med., 1082 (1987); Soc. of Nuc. Med., Reston, VA.
Renkin, E. M., "Transport of potassium–42 from blood to tissue in isolated mammalian skeletal muscles," 197, Am J. Physiol., 1205–1210 (1959); Am. Physiol. Soc., Bethesda, MD.
Roberts, A. D., et al., "Production of 17F, 15O and Other Radioisotopes for PET using a 3 MV Electrostatic Tandem Accelerator," 475, Applications of Accelerators in Res. and Indus., 1006–1009 (1999); Med. Physics & Psych. Depts., UW–Madison.
Roberts, A. D., et al., "Posterboard 1074," Proceedings of the 47th Annual Meeting, 41 (5), J. Nuc. Med., 243 (2000); Soc. of Nuc. Med., Reston, VA.
Roberts, A. D., et al., "Production of the Short–Lived Flow Tracer Fluorine–17 Fluoromethane From Proton Irradiation of Neon," Posters for Poster Presentation, 47th Annual Meeting of Society of Nuclear Medicine, St. Louis, Missouri, Jun. 3–7, 2000; Dep't. of Med. Phys., UW–Madison.
Sheppard, W. A., et al., Organic Fluorine Chemistry, pp. 56 and 93 (W. A. Benjamin, Inc., New York, 1969).

* cited by examiner

Primary Examiner—Michael G. Hartley
(74) Attorney, Agent, or Firm—Foley & Lardner

(57) ABSTRACT

Fluoroalkanes such as fluoromethane labeled with $^{17}F$ are produced by contacting $^{17}F$ labeled $F_2$ with alkanes, preferably methane, substituted or unsubstituted alkenes, or substituted or unsubstituted alkynes in the presence of a metal oxide catalyst, preferably a silver oxide catalyst, to produce the $^{17}F$ labeled fluoroalkane. The $^{17}F$ may be produced by irradiating $^{20}Ne$ with protons, preferably having an energy of about 11 MeV and produced by a cyclotron. The $^{17}F$ labeled fluoromethane or fluoroalkanes may be produced continuously. A method for determining the location of an $^{17}F$ labeled tracer includes generating an $^{17}F$ labeled fluoroalkane, administering the $^{17}F$ labeled fluoroalkane to a test subject, and scanning the test subject with a radiosensitive detector such as a positron emission tomography scanner.

34 Claims, 7 Drawing Sheets

US 6,585,953 B2

SYNTHESIS OF 17F LABELED FLUOROALKANES

CROSS REFERENCES TO RELATED APPLICATIONS

This application claims priority to U.S. Provisional Application No. 60/230,780, filed Sep. 7, 2000, the entire disclosure of which is incorporated herein by reference.

GOVERNMENT RIGHTS

This invention was made with United States government support awarded by the following agency: NIMH P50 MH52354. The United States has certain rights in this invention.

FIELD OF THE INVENTION

This invention pertains generally to the production of $^{17}$F and to the synthesis of $^{17}$F labeled fluoromethane and other fluoroalkanes and the use of such labeled materials in positron emission tomography.

BACKGROUND OF THE INVENTION

Positron emission tomography (PET) has found wide application as a diagnostic method. Various radioisotopes have been investigated for application in PET and other diagnostic imaging methods. One of these radioisotopes is $^{15}$O $^{15}$O (t½=122 seconds) tracers such as $^{15}$O labeled water are currently the most commonly used tracers in PET. One advantage of $^{15}$O labeled water as a tracer is that it can be easily and reliably synthesized. A disadvantage, however, is that it has a relatively low permeability surface product such that at high flows, the signal is reduced. Eichling et al. *Circ. Res.* 35, 358–364 (1974); Herscovitch et al. *J. Cereb. Blood Flow Metab.* 7, 527–542 (1987); Renkin, E. M. *Am J. Physiol.* 197, 1205–1210 (1959). Additionally, tracers such as $^{15}$O labeled water are usually administered by injection and are slow to clear test subjects.

Another radioisotope that has been used is $^{18}$F (t½=110 minutes) in tracers such as $^{18}$F labeled fluoromethane which has been used to determine regional cerebral blood flow (rBCF). Gatley, et al. *Int. J. Appl. Radiat. Isot.* 32, 211–214, (1981). Because of the relatively long half life of $^{18}$F, tracers labeled with this isotope are ill suited for the fast repetitions necessary for cerebral activation protocols.

The short half life of $^{17}$F ($E_\beta^+$(max)=1.74 MeV; t½≈64 seconds) suggests that this might be a suitable radioisotope for use in PET. The short half life presents problems, however, in that tracers labeled with this isotope must be prepared quickly in order to preserve the maximum amount of $^{17}$F in a labeled compound.

$^{17}$F labeled fluoromethane has been prepared by several routes. For example, $^{17}$F labeled fluoromethane has reportedly been produced by Hunsdiecker like decomposition of $^{17}$F acetyl hypofluorite and by passage of $^{17}$F labeled F$_2$ through CH$_3$HgCl. Mulholland et al. *J. Nuc. Med* 28, 1082, (1987). These methods do not produce $^{17}$F labeled fluoromethane in sufficient yield for practical imaging use.

Therefore, a need exits for an improved method of generating $^{17}$F and for producing labeled fluoromethane and other fluoroalkanes from it. A need also remains for improved diagnostic methods using $^{17}$F labeled fluoromethane and other fluoroalkanes.

SUMMARY OF THE INVENTION

The present invention provides $^{17}$F labeled fluoromethane and other $^{17}$F labeled fluoroalkanes, and methods for producing $^{17}$F labeled fluoromethane and other $^{17}$F labeled fluoroalkanes. The invention also provides methods of determining the location of an $^{17}$F labeled tracer.

A method of generating $^{17}$F labeled fluoroalkanes includes contacting $^{17}$F labeled F$_2$ with an alkane, preferably methane, a substituted or unsubstituted alkene, or a substituted or unsubstituted alkyne in the presence of a metal oxide catalyst to produce the $^{17}$F labeled fluoroalkane. In more preferred embodiments, the $^{17}$F labeled F$_2$ is contacted with the alkane, the substituted or unsubstituted alkene, or the substituted or unsubstituted alkyne in the presence of the metal oxide catalyst and neon.

In preferred embodiments, the $^{17}$F is generated by proton irradiation of $^{20}$Ne in a target gas stream comprising neon, preferably natural neon gas. In still other embodiments, the target gas stream includes F$_2$ and neon gas that includes $^{20}$Ne whereas in still other preferred embodiments, the target gas stream includes helium, F$_2$, and neon gas that includes $^{20}$Ne.

In preferred embodiments, the $^{20}$Ne is irradiated with protons having an energy of greater than 8 MeV, more preferably with an energy of about 11 MeV. In another preferred embodiment the protons have an energy of about 16 MeV. The protons used to irradiate $^{20}$Ne are preferably generated by a cyclotron.

In another embodiment, the $^{17}$F is generated by deuteron irradiation of $^{16}$O in a target gas stream that includes O$_2$.

In preferred processes, the target gas stream preferably comprises less than or about 1.0 percent, more preferably less than about 0.7 percent, and most preferably less than about 0.3 percent of F$_2$. In still other preferred embodiments the total pressure of the target gas ranges from about 100 to about 400 psig or more preferably ranges from about 160 to about 240 psig.

In other preferred embodiments of producing $^{17}$F labeled fluoromethane, the $^{17}$F labeled F$_2$ is contacted with methane, and the metal oxide catalyst is silver oxide, preferably at a temperature ranging from about 200° C. to about 600° C. More preferably, the metal oxide is at a temperature ranging from about 400° C. to about 500° C., and most preferably the metal oxide is at a temperature of about 450° C.

In other more preferred embodiments of producing $^{17}$F labeled fluoroalkanes, the $^{17}$F labeled F$_2$ is contacted with the substituted or unsubstituted alkene or the substituted or unsubstituted alkyne and the metal oxide catalyst is silver oxide which is more preferably at a temperature ranging from about 10° C. to about 600° C. or still more preferably is at a temperature ranging from about 20° C. to about 100° C. Most preferably, the metal oxide catalyst is at a temperature of about 25° C. in the process for producing $^{17}$F labeled fluoroalkanes.

In still other preferred embodiments, the alkene or alkyne contacted with the $^{17}$F labeled F$_2$ is a haloalkene or haloalkyne, more preferably a fluorinated alkene or alkyne. Still more preferably, the alkene is a difluoroalkene, yet more preferably 1,1-difluoroethylene such that the $^{17}$F labeled fluoroalkane produced is $^{17}$F labeled 1,1,1,2-tetrafluoroethane where one of the fluorine atoms is an $^{17}$F fluorine atom.

In still other preferred embodiments, the $^{17}$F labeled fluoroalkane is passed through a scrubber, preferably a soda lime scrubber.

In yet other preferred embodiments of the method of generating the $^{17}$F labeled fluoroalkane, the $^{17}$F is continuously generated by continuously irradiating the target gas stream with protons and the $^{17}$F labeled fluoroalkane is continuously produced by continuously contacting the $^{17}$F labeled $F_2$ with the alkane, the substituted or unsubstituted alkene, or the substituted or unsubstituted alkyne, more preferably methane.

A method of determining the location of an $^{17}$F labeled tracer is also provided. The method includes generating the $^{17}$F labeled fluoroalkane according to the invention; administering the $^{17}$F labeled fluoroalkane to a test subject; and collecting scans of the test subject using a radiosensitive detector. In preferred such methods, the $^{17}$F labeled fluoroalkane is administered to the test subject by having the test subject inhale the $^{17}$F labeled fluoroalkane. In another preferred method of determining the location of an $^{17}$F labeled tracer, the $^{17}$F labeled fluoroalkane is added to a saline solution and the saline solution is administered to the test subject.

Preferred radiosensitive detectors for use in determining the location of an $^{17}$F labeled tracer such as $^{17}$F labeled fluoromethane and other $^{17}$F labeled fluoroalkanes, are selected from a scintillation detector, a Geiger counter, a positron emission tomography scanner, a single photon emission computed tomography scanner, or a solid state detector. More preferred radiosensitive detectors for use in the method of determining the location of an $^{17}$F labeled tracer are positron emission tomography scanners or cameras.

In other more preferred embodiments of producing $^{17}$F labeled fluoroalkanes, the $^{17}$F labeled $F_2$ is contacted with the substituted or unsubstituted alkene or the substituted or unsubstituted alkyne and the metal oxide catalyst is silver oxide which is more preferably at a temperature ranging from about 10° C. to about 600° C. or still more preferably is at a temperature ranging from about 20° C. to about 100° C. Most preferably, the metal oxide catalyst is at a temperature of about 25° C. in the process for producing $^{17}$F labeled fluoroalkanes.

In still other preferred embodiments, the alkene or alkyne contacted with the $^{17}$F labeled $F_2$ is a haloalkene or haloalkyne, more preferably a fluorinated alkene or alkyne. Still more preferably, the alkene is a difluoroalkene, yet more preferably 1,1-difluoroethylene such that the $^{17}$F labeled fluoroalkane produced is $^{17}$F labeled 1,1,1,2-tetrafluoroethane where one of the fluorine atoms is an $^{17}$F fluorine atom.

The invention also provides the $^{17}$F labeled fluoromethane and fluoroalkanes produced by the processes of the invention.

$^{17}$F labeled organic compounds are provided and include $^{17}$F labeled fluoromethane and an $^{17}$F labeled alkane having more than 2 carbon atoms. In more preferred $^{17}$F labeled organic compounds, the alkane comprises at least two fluorine atoms and at least one of the fluorine atoms is an $^{17}$F. In still other more preferred $^{17}$F labeled organic compounds, the $^{17}$F labeled alkane is 1,1,1,2-tetrafluoroethane where at least one of the F atoms is an $^{17}$F fluorine atom.

The invention still further provides gaseous compositions that include $^{17}$F labeled fluoromethane that has an equilibrium activity of greater than or about 20 mCi. In some preferred embodiments, the equilibrium activity level is greater than or about 40 mCi whereas in still other preferred embodiments, the equilibrium activity level is greater than or about 70 mCi.

Further objects, features and advantages of the invention will be apparent from the following detailed description when taken in conjunction with the accompanying drawings.

BRIEF DESCRIPTION OF THE DRAWINGS

In the drawings like numerals represent like elements.

DETAILED DESCRIPTION OF THE INVENTION

Figure 1:
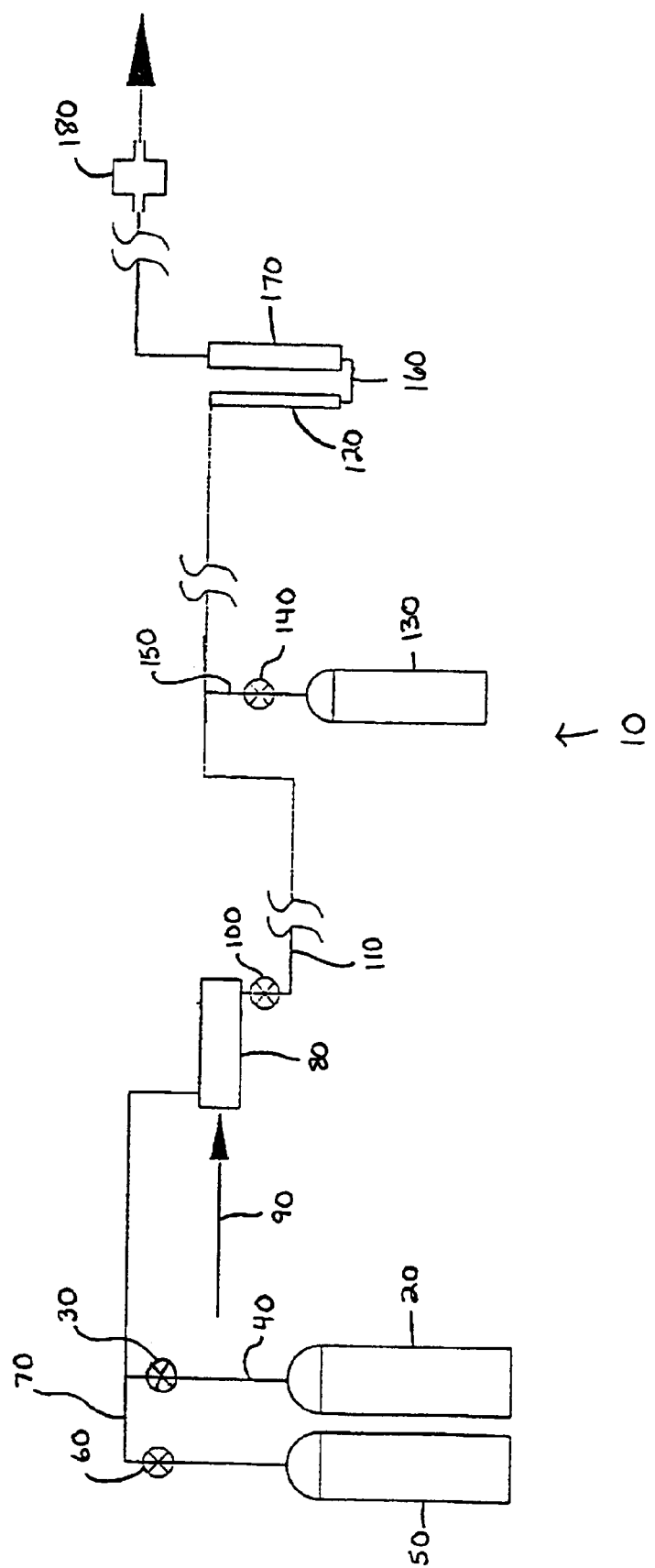
FIG. 1 is a schematic diagram illustrating various parts of an apparatus used for the continuous production of $^{17}$F labeled fluoromethane and other $^{17}$F labeled fluoroalkanes.

Generally, the invention provides $^{17}$F labeled fluoromethane and other $^{17}$F labeled fluoroalkanes, methods for producing $^{17}$F labeled fluoromethane and other $^{17}$F labeled fluoroalkanes, and methods of determining the location of a $^{17}$F labeled tracer such as with a positron emission tomography scanner.

All ranges recited herein include all combinations and subcombinations included within that range's limits. Therefore, a temperature range of from about 200° C. to about 600° C. includes ranges of from 200° C. to 600° C., of from 300° C. to 600° C., of from 250° C. to 500° C., of from 225° C. to 425° C., etc.

Positron emitting $^{17}$F ($E_\beta^+$(max)=1.74 MeV; t½≈64 seconds) has an ideal half life for probing such diverse processes as gray matter cerebral activity or gas-phase reactions on an industrial scale. Because of the very short half life of $^{17}$F, tracers labeled with this isotope such as $^{17}$F labeled fluoromethane provide very short half life cerebral blood flow agents that have important application in PET studies of seizure and other transient brain phenomena. The shorter half life of $^{17}$F with respect to $^{15}$O permits repeat images to be obtained twice as fast with $^{17}$F labeled tracers as compared to $^{15}$O labeled tracers such as water which is presently in wide use as a tracer as described above. The ability to scan twice as fast using $^{17}$F labeled tracers allows more data to be collected in the same amount of time and should allow more test subjects to be evaluated using instruments that are currently in high demand. Additionally, $^{17}$F labeled tracers show improved signal to noise level ratios over $^{15}$O labeled tracers providing increased sensitivity. $^{15}$O tracers such as $^{15}$O labeled water are usually administered in a manner that is more invasive than are tracers such as $^{17}$F labeled fluoromethane. For example, $^{15}$O labeled tracers are usually administered by injection and arterial measurements are then made from an arterial cannulation. On the other hand, $^{17}F$ labeled tracers such as fluoromethane may be administered by having a test subject inhale the tracer, and arterial measurements can be made from exhalations. Furthermore, tracers such as $^{17}F$ labeled fluoromethane are rapidly cleared by exhalation and the biological half life is quite short.

Two nuclear reactions may be used to generate $^{17}F$ in practical yields for use in the present invention. First, and preferably, $^{17}F$ may be produced by the irradiation of $^{20}Ne$ in a nuclear reaction that may be written as $^{20}Ne(p,\alpha)^{17}F$ with A(EOSB) of 14 mCi/$\mu$A leaving the target with an $E_p$ equal to 11 MeV where EOSB stands for end of saturation bombardment. $^{17}F$ may also be produced by the deuteron irradiation of $^{16}O$ in natural or other $O_2$ in a process that may be written $^{16}O(d,n)^{17}F$ with A(EOSB) of 125 mCi/$\mu$A and an $E_d$ value of 11 MeV. Addition of small amounts of $F_2$ to either target gas has been found to bring the $^{17}F$ activity quantitatively out of the aluminum target. The production of $^{17}F$ by proton irradiation of $^{20}Ne$ has several advantages over the production by deuteron irradiation of $^{16}O$. First, the $^{17}F$ is produced in an inert gas for improved fast radiochemistry. Second, production of $^{17}F$ by proton irradiation of $^{20}Ne$ is readily implementable using low energy proton cyclotrons. The $^{20}Ne$ is generally supplied as a component of natural neon which refers to neon gas having various isotopes and which is the type of neon commonly available and sold in gas cylinders. Similarly, natural $O_2$ refers to oxygen that is readily available and sold in standard gas cylinders and is found as a component in the earth's atmosphere.

Because of the relatively short half life of $^{17}F$, tracers labeled with this radioisotope must be prepared quickly to maintain optimal levels of $^{17}F$ in the tracer. $^{17}F$ labeled fluoromethane, [$^{17}F$]CH$_3$F, may be conveniently and quickly generated by contacting methane, methyl bromide, methyl chloride, or methyl iodide with $^{17}F$ labeled $F_2$ in the presence of a metal oxide catalyst, preferably a silver oxide catalyst. More preferably, $^{17}F$ labeled fluoroalkanes are prepared by contacting $^{17}F$ labeled $F_2$ with methane or other alkanes in the presence of a metal oxide catalyst where the metal oxide is at a temperature ranging from about 200° C. to about 600° C. or still more preferably at a temperature of from about 400° C. to about 500° C. or yet more preferably at a temperature of about 450° C. Alkanes that may be used to prepare $^{17}F$ labeled fluoroalkanes include linear, branched chain, and cyclic alkanes. Examples of such alkanes other than methane include, but are not limited to, ethane, propane, cyclopropane, butane, cyclobutane, methylcyclopropane, 2-methylpropane, 2-methylbutane, 2,3-dimethylbutane, methylcyclobutane, pentane, cyclopentane, hexane, methylcyclopentane, cyclohexane, and mixtures thereof.

Other $^{17}F$ labeled fluoroalkanes may be generated by contacting $^{17}F$ labeled $F_2$ with a substituted or unsubstituted alkene or alkyne with a metal oxide catalyst, preferably a silver oxide catalyst. In such processes, the metal oxide catalyst is preferably at a temperature ranging from about 10° C. to about 600° C. or more preferably is at a temperature of from about 20° C. to about 100° C. Most preferably in processes using alkenes or alkynes, the metal oxide catalyst is at a temperature of about 25° C. In particular, the preparation of a $^{17}F$ labeled 1,1,1,2-tetrafluoroalkane may be accomplished by contacting $^{17}F$ labeled $F_2$ with 1,1-difluoroethylene in the presence of the metal oxide catalyst. The $^{17}F$ labeled fluoromethane and other fluoroalkanes may be used as tracer compounds in positron emission tomography and in the study of industrial gases such as 1,1,1,2-tetrafluoroethane-a commercially important refrigerant. The process for generating $^{17}F$ labeled $F_2$, $^{17}F$ labeled fluoromethane, and other $^{17}F$ labeled fluoroalkanes is better explained with reference to FIG. 1.

FIG. 1 is a schematic diagram of an apparatus 10 that may be used in the continuous production of $^{17}F$ labeled fluoromethane and other $^{17}F$ labeled fluoroalkanes. As shown in FIG. 1, the target gas, preferably $^{20}Ne$ in natural neon gas, is supplied to the system from a target gas cylinder 20 with a metering valve 30 through line 40 whereas $F_2$ is supplied to the system from a gas cylinder 50 with a metering valve 60 through line 70. The $F_2$ is most preferably supplied as a component of a gas mixture so that it is in a diluted rather than in a pure form. Thus, gas cylinder 50 generally supplies a mixture of gases to the system where less than about 5 percent of the gas mixture is $F_2$. In one preferred embodiment, the remainder of gas in cylinder 50 is an inert gas such as helium. In another preferred embodiment the remainder of gas in cylinder 50 is neon. The target gas from cylinder 20 is mixed with the gas mixture from cylinder 50 forming a target gas stream which flows through line 70 to target 80 shown in greater detail in FIG. 2.

One skilled in the art will recognize that it is not necessary that the $F_2$ and neon be supplied to the target 80 from separate sources. For example, in a highly preferred embodiment, a mixture of neon and $F_2$ is used to supply the target gas such that the target gas in cylinder 20 comprises $F_2$ and a species to be irradiated, preferably $^{20}Ne$ in natural neon gas. Thus, in a highly preferred process, cylinder 20 comprises $F_2$ and natural neon which includes $^{20}Ne$ as one of its component isotopes of Ne. No helium is required or necessary in such a process although it may certainly be present without deleterious effect on the process.

The target gas stream preferably includes $^{20}Ne$ and $F_2$ and more preferably includes $^{20}Ne$, $F_2$, and helium in one embodiment. Most preferably, as described above, the target gas stream comprises $F_2$ and natural neon gas that includes $^{20}Ne$ among other isotopes of Ne. The target gas stream generally is less than about 3.0 percent $F_2$. In most processes, however, the target gas stream is less than 1.0 percent $F_2$, is more preferably less than about 0.7 percent $F_2$, and is still more preferably less than about 0.3 percent $F_2$ although those skilled in the art will recognize that various levels of $F_2$ may be used in the process of the invention. The percentage of neon and helium in a target gas stream may vary considerably. Generally, when helium is present in the target gas stream, the percentage of neon in the target gas stream is greater than 70 percent. More preferably in helium-containing gas streams, however, the percentage of neon in the target gas stream is greater than about 85 percent. Still more preferably in helium-containing target streams, the percentage of neon in the target gas stream is greater than or about 87 percent with helium and $F_2$ making up the remainder of such target gas streams.

In preferred processes which do not use helium, but rather consist essentially of neon and $F_2$, the percentage of neon in the target gas stream is greater than 97 percent. In more preferred such processes, the percentage of neon in the target gas stream is greater than about 98 percent. In still more preferred such processes, the percentage of neon in the target gas stream is greater than about 99 percent, and still more preferably is greater than about 99.5 percent.

The pressure of the target gas stream preferably ranges from about 100 to about 400 psig although those skilled in the art will recognize that the target gas stream may be at pressures outside this range. More preferably, the total pressure of the target gas stream ranges from about 120 to about 300 psig, and still more preferably ranges from about 160 to about 240 psig. The flow rate of the target gas stream into target 80 may vary considerably, but is typically maintained at a range of from about 100 to about 300 mL/minute. More preferably, the flow rate is maintained at from about 130 to about 220 mL/minute.

In the target 80, the target gas mixture is irradiated with a stream of protons 90 having an energy of greater than 8 MeV, preferably having an energy of about 11 MeV and supplied by a cyclotron such as a CTI-RDS-112cyclotron (not shown) or having an energy of about 16 MeV and supplied by a cyclotron such as a PET Trace cyclotron available from General Electric. Irradiation of $^{20}$Ne with the protons produces $^{17}$F and gives rise to the $^{17}$F labeled $F_2$ used to produce $^{17}$F labeled fluoromethane and other $^{17}$F labeled fluoroalkanes.

After leaving target 80, a metering valve 100 is used to regulate the flow of the $^{17}$F labeled $F_2$ containing gas stream which moves through line 110 to a column 120 containing a metal oxide catalyst. Metal oxide catalysts for use in the process include, but are not limited to copper oxide, nickel oxide, and silver oxide with silver oxide being a highly preferred metal oxide catalyst. Prior to entering column 120, a reactant gas supplied from cylinder 130 and regulated with metering valve 140 is added to the gas stream containing the $^{17}$F labeled $F_2$ through line 150. Because the gas stream contains neon, the reactant gas preferably contacts the $^{17}$F labeled $F_2$ in the presence of the metal oxide catalyst and neon. For producing $^{17}$F labeled fluoromethane, the reactant gas in cylinder 130 is preferably methane, methyl bromide, methyl chloride, or methyl iodide, but is most preferably methane. For producing other $^{17}$F labeled fluoroalkanes, the reactant gas is preferably a substituted or unsubstituted alkene or alkyne such as, but not limited to substituted or unsubstituted ethylene, propylene, 1-butene, 2-butene, pentenes, hexenes, cyclopentene, cyclohexene, acetylene, 1-propyne, 1-butyne, 2-butyne, pentynes, or hexynes. The alkenes or alkynes are preferably haloalkenes or haloalkynes and are more preferably fluoroalkenes or alkynes such as difluoroalkenes. An example of a particularly preferred substituted alkene is 1,1-difluoroethylene which reacts with $^{17}$F labeled $F_2$ to produce $^{17}$F labeled 1,1,1,2-tetrafluoroethane.

As described above, for the production of fluoromethane, the metal oxide catalyst is preferably at a temperature ranging from about 200° C. to about 600° C., more preferably ranging from about 400° C. to about 500° C., and most preferably is at a temperature of about 450° C. When the reactant gas is a substituted or unsubstituted alkene or alkyne, the metal oxide is preferably at a temperature ranging from about 10° C. to about 600° C., but is more preferably at a temperature ranging from about 20° C. to about 100° C. Most preferably, when the reactant gas is a substituted or unsubstituted alkene or alkyne, the temperature of the metal oxide catalyst is about 25° C. or room temperature. The column containing the metal oxide catalyst may be heated, if desired, using any conventional means known to those skilled in the art such as heating tape or coils.

The reactant gas from cylinder 130 may be added to the gas stream containing the $^{17}$F labeled $F_2$ at various flow rates which will be recognized by those skilled in the art. However preferred flow rates generally range from about 1 to about 10 mL/minute. A particularly preferred flow rate for the reactant gas is a rate of about 3 mL/minute. The reactant gas may be added to the system in a pure or diluted form. For example, methane may be added in a pure form or as a mixture with an inert gas such as helium or neon.

As described above, the $^{17}$F labeled $F_2$ preferably contacts the reactant gas in the presence of the metal oxide catalyst while in column 120. After passing through column 120, the product stream containing the $^{17}$F labeled fluoromethane or other fluoroalkane passes through line 160. Line 160 preferably passes through a scrubber 170 such as a soda lime scrubber or trap to remove $F_2$ and HF from the $^{17}$F labeled fluoromethane or other $^{17}$F labeled fluoroalkane. Tests with KI indicator strips showed that no detectable $F_2$ remained in the stream following the soda lime scrubber. Other separation devices such as filter 180, can be used to remove mass contaminants to undetectable levels. One such preferred type of filter is a Waters Sep-Pak Plus C18 cartridge filter.

Typical production using the procedure and apparatus set forth above with protons having an energy of about 11 MeV at a 10–15 $\mu$A beam provided 100 to 150 mCi of $^{17}$F labeled $F_2$, and 35 to 50 mCi of $^{17}$F fluoromethane when methane was used as the reactant gas. The process may be used to prepare gaseous compositions that include $^{17}$F labeled fluoromethane and have an equilibrium activity of greater than or about 20 mCi, of greater than or about 40 mCi, or of greater than or about 70 mCi. Such gaseous compositions generally will also contain neon or mixtures of neon and helium.

Using the apparatus described above, $^{17}$F labeled fluoromethane was produced in yields approaching the theoretical maximum of 50 percent by the addition of methane at approximately 2 percent to a target stream containing neon, helium and 0.5 percent $F_2$ after the target stream had been irradiated with protons and the resulting mixture containing methane had been passed through a column of powdered silver oxide at 450° C. Gas chromatography (Porpak Q column; He carrier gas; thermal conductivity detector, electrochemical detector, and positron coincidence radiation detector) indicated that the radiochemical purity of [$^{17}$F]$CH_3F$ was greater than 90 percent with less than a 100 ppm [$^{18}$F]$CH_3F$ radionuclidic contaminant. With approximately 10 $\mu$A of 11 MeV protons on target, continuous gas flow saturated the ballast reservoir at 44 mCi at a PET scanner located 20 meters away. Anesthetized primates drawing from this continuously replenished supply of $^{17}$F labeled fluoromethane exhibited a cerebral counting rate that rapidly reached a plateau of 100 kcps (7 slices, 52 mm axial field of view, 2D, CTI 933/04 PET camera). This permitted megacount flow images in a minute. The end expiratory concentration of $CH_3^{17}F$ was monitored by a flow-through beta detector, and provided the arterial concentration sufficient for quantifying regional cerebral blood flow.

Using the apparatus described above, $^{17}$F labeled 1,1,1, 2-tetrafluoroethane was produced almost quantitatively by reaction of $^{17}$F labeled $F_2$ with 1,1-difluoroethylene in the gas-jet reaction over silver oxide at room temperature. The radiochemical purity was found to be in excess of 80 percent as determined by gas chromatography.

The neon gas used in the apparatus described above was CP grade and obtained from Air Products. The $F_2$ was obtained as a gas mixture of 5 percent $F_2$ in helium from Air Products. Monel brand and stainless steel Swagelok brand fittings were used. Valves used in the apparatus included Nupro brand (M- or SS- BG or BK valves, Whitey brand SS-41S1 and 41XS1 valves, and Swagelok brand SS-S1 valves. The tubing of the various lines was typically 1/16 inch stainless steel or polytetrafluoroethylene (PTFE). The target used was that shown in FIG. 2.

As described above, FIG. 2 shows one target 80 that may be used to generate $^{17}$F labeled $F_2$ from $^{20}$Ne in a target gas stream. The target 80 includes an aluminum housing 190 and an aluminum end flange 200 secured to housing 190 with screws 210. Aluminum end flange 200 defines an inlet 220 through which the target gas stream is introduced into the interior of housing 190. Inlet fitting 230 is used to connect target 80 to a feed gas supplied through line 70. On the other end of target 80 is the double foil cooling and target mount assembly 240 which secures target 80. The target 80 is cooled with a water cooling line 250. Viton® brand O-rings 260 are used to seal target 80. In operation, protons generated by the cyclotron (not shown) enter the interior of the housing 190 of target 80 through Havar foil 270 of about 0.0012 inch thickness. The protons irradiate the $^{20}$Ne in the interior of target 80 and convert $^{20}$Ne into $^{17}$F which subsequently forms $^{17}$F labeled $F_2$. The gaseous product leaves target 80 by passing through gas outlet 255 which has a diameter of about 0.040 inches. The gaseous product then continues to a stainless steel gas exit tube 265 held onto target 80 by a flange 270 and O-rings 280. An outlet fitting 290 connects gas exit tube 265 to line 110 which directs the $^{17}$F labeled $F_2$ containing stream to column 120. A metering valve may be used to control the flow of gas from target 80 into line 110.

Figure 2:
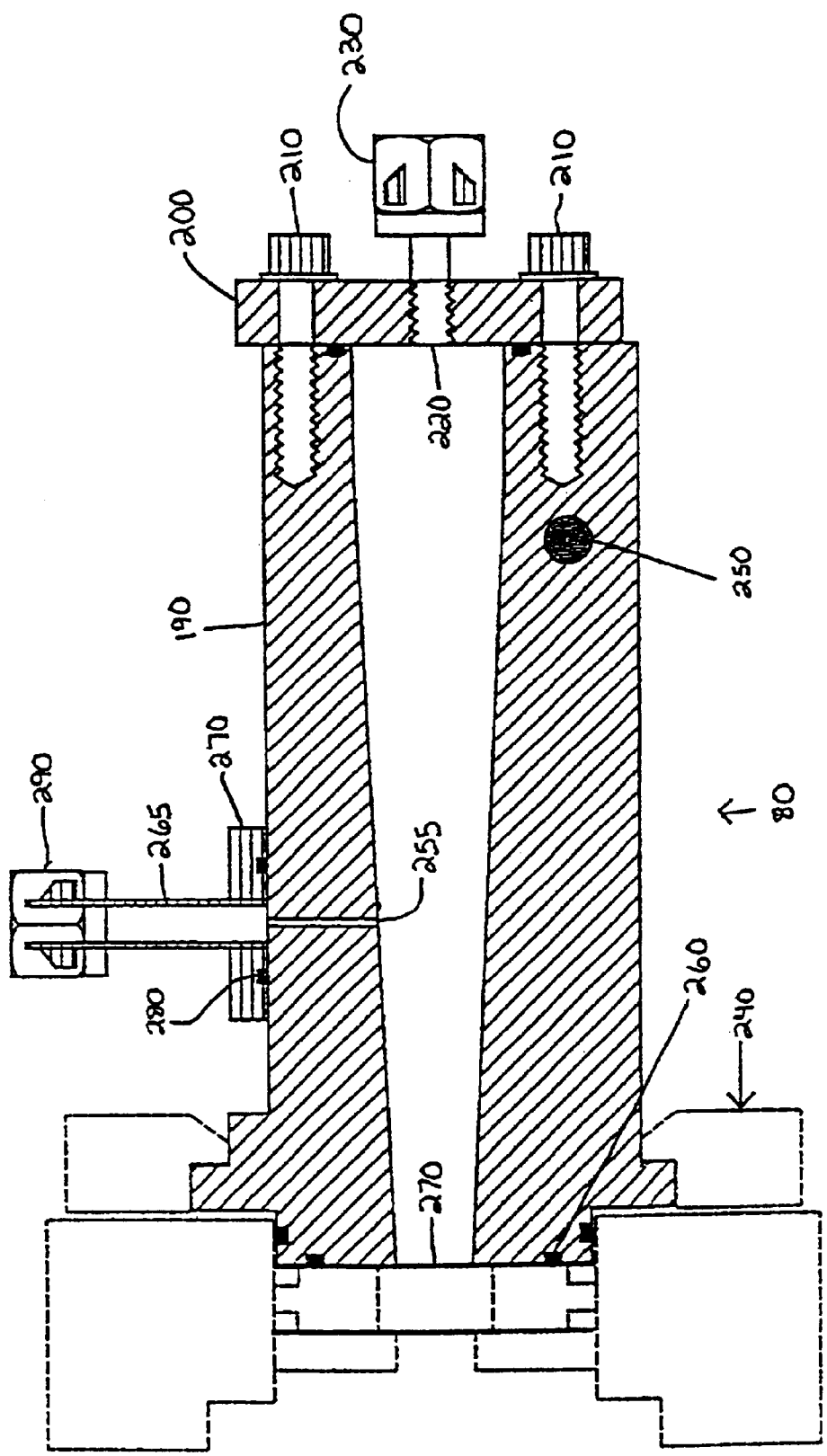
FIG. 2 is a diagram of a production target in which $^{17}$F labeled $F_2$ is produced.

One skilled in the art will recognize that other flow through target geometries may be used to generate the $^{17}$F in the process of the invention. Thus, the choice of a target such as that shown in FIG. 2 is not critical to the processes for preparing $^{17}$F labeled $F_2$, $^{17}$F labeled fluoromethane, or other fluoroalkanes.

Additionally, one skilled in the art will recognize that $^{17}$F labeled $F_2$ may be produced by deuteron irradiation of $^{16}$O as described above. In such a system, neon is not necessary, but the remainder of the system is similar to that described in FIG. 1. In a system using $^{16}$O and deuteron bombardment to produce $^{17}$F labeled $F_2$, a mixture of $F_2$ and $O_2$, preferably natural $O_2$ gas, is supplied to a target and then irradiated with deuterons having an energy of greater than 1 MeV. In such a system, the gas stream leaving the target would include $^{17}$F labeled $F_2$ and $O_2$ which would then proceed to column 120 containing the metal oxide catalyst.

Figure 3:
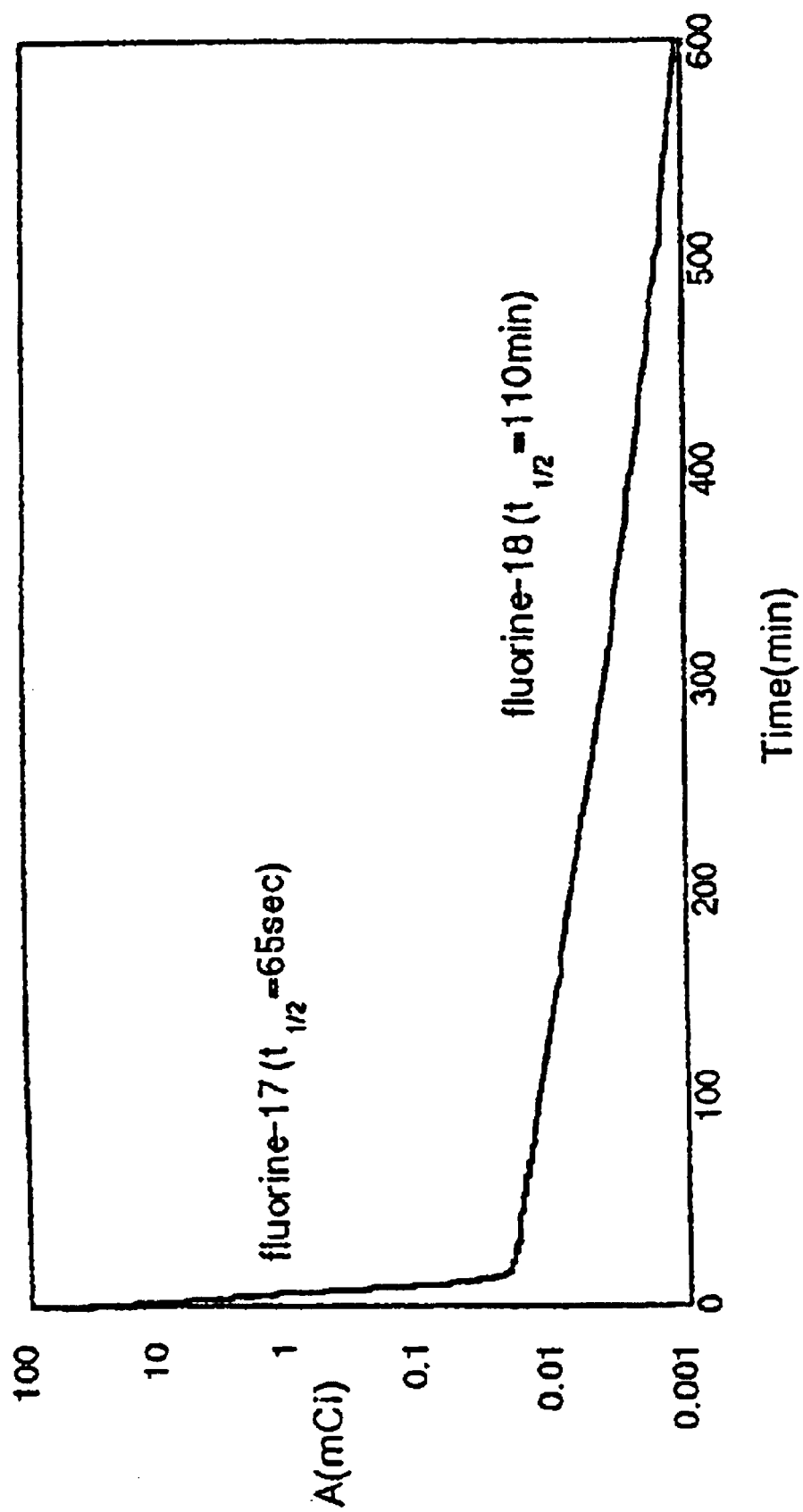
FIG. 3 is a graph showing the decay of $^{17}$F as a function of time and the decay of the small amount of $^{18}$F produced as the only radionuclidic impurity.

FIG. 3 is a graph showing the decay of $^{17}$F as a function of time. The decay analysis of $^{17}$F labeled $F_2$ was performed after 5 minutes and 15 $\mu$A irradiation under standard flow conditions. The calculated $^{18}$F/$^{17}$F number ratio in the gas stream was determined to be $3\times10^{-5}$, resulting in approximately 0.2 mCi total $^{18}$F buildup in a 60 minute experiment under these conditions, compared to the equilibrium 150–175 mCi $^{17}$F.

Figure 4:
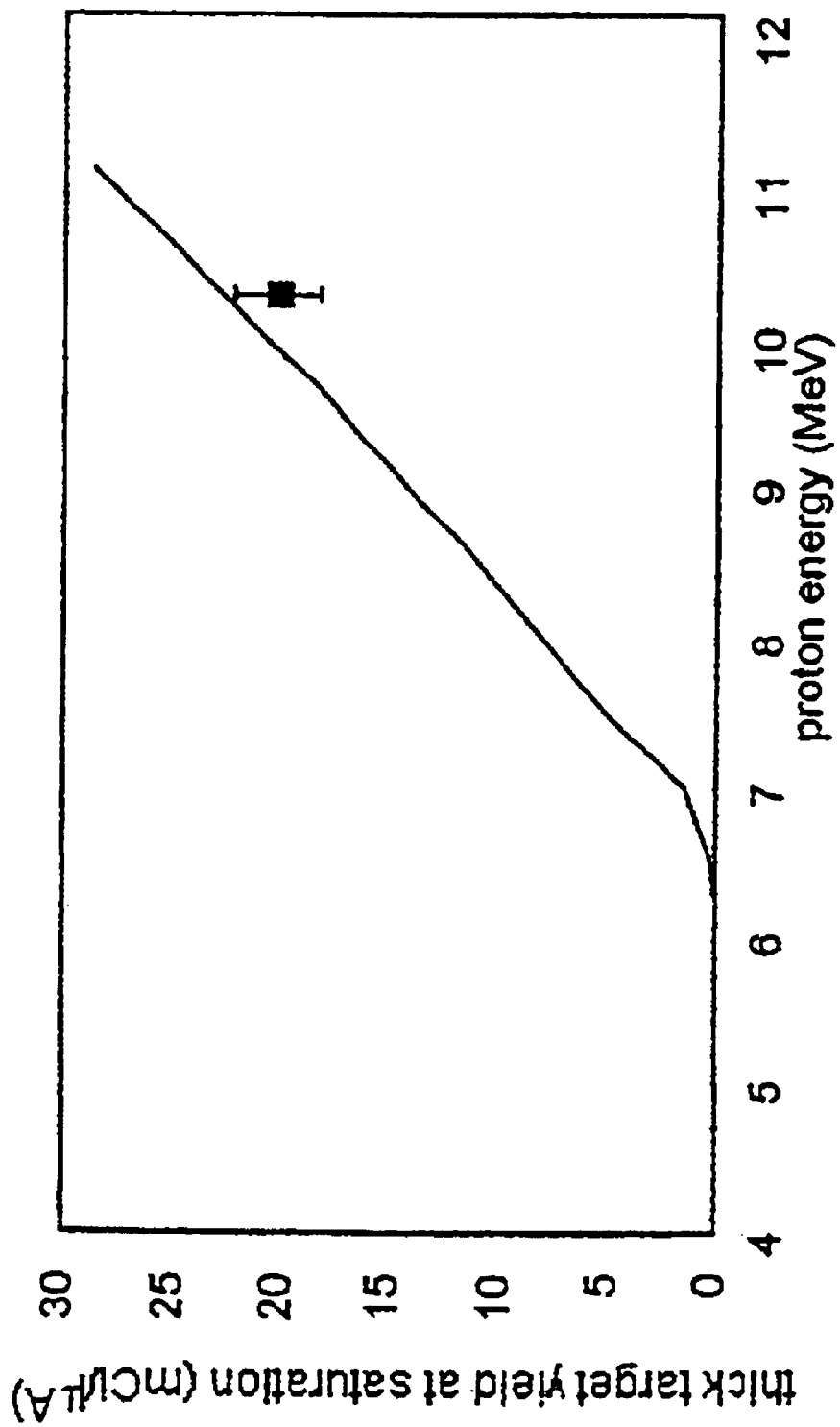
FIG. 4 is a graph comparing the thick target yield for $^{20}$Ne(p,α)$^{17}$F calculated from published total cross section data (Gruhle W., Kober B., *Nuclear Physics*, A286, 1, 523–530 (1977)) and the measured yield using a CTI-RDS-112 cyclotron 11 MeV proton beam.

FIG. 4 is a graph comparing the thick target yield for $^{20}$Ne(p,$\alpha$)$^{17}$F calculated from published total cross section data (Gruhle W., Kober B., Nuclear Physics, A286, 1, 523–530 (1977)) and the measured yield using a CTI-RDS-112 cyclotron 11 MeV proton beam. The measured yield of about 20 mCi/$\mu$A is corrected for transport decay (12 seconds), neon fraction in target gas (87%), and natural $^{20}$Ne fraction (90.5%)

Figure 5:
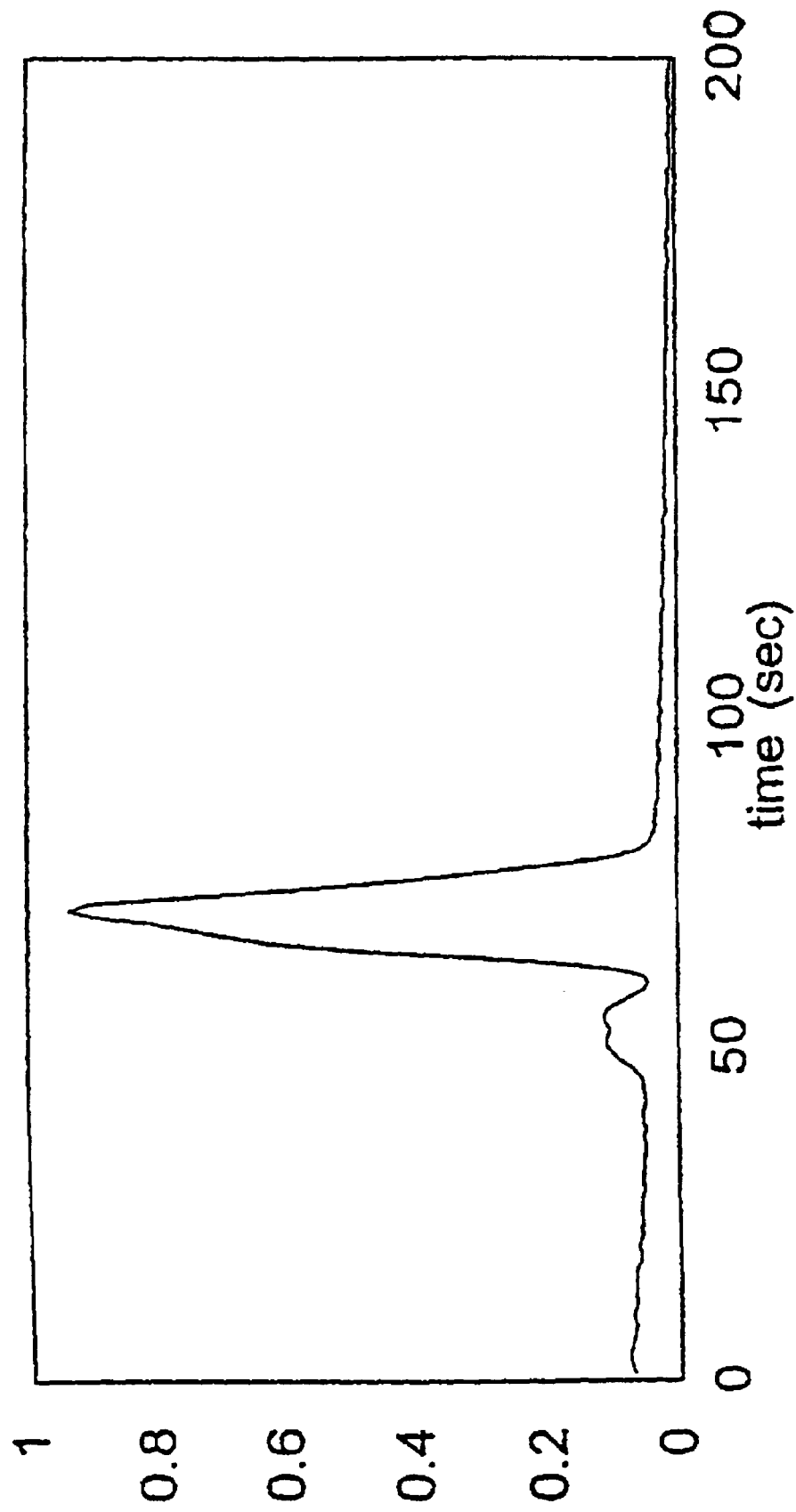
FIG. 5 is a gas chromatograph showing the radiochemical purity of $^{17}$F labeled fluoromethane where the large peak represents $^{17}$F labeled fluoromethane and the small peak represents $^{17}$F labeled $CF_4$ from the target as a radiochemical impurity.

FIG. 5 is a gas chromatograph (Porpak Q column; He carrier gas; thermal conductivity detector, electrochemical detector, and positron coincidence radiation detector) showing the radiochemical purity of $^{17}$F labeled fluoromethane produced by the present invention. The radiochemical purity of the $^{17}$F labeled fluoromethane was determined to be 91 percent with only $^{17}$F labeled $CF_4$ from the target as a radiochemical impurity. Notably, when used as a tracer, $CF_4$ stays out of the blood when inhaled. Thus, the presence of $CF_4$ only impacts the dosimetry to the lungs and trachea.

Figure 6:
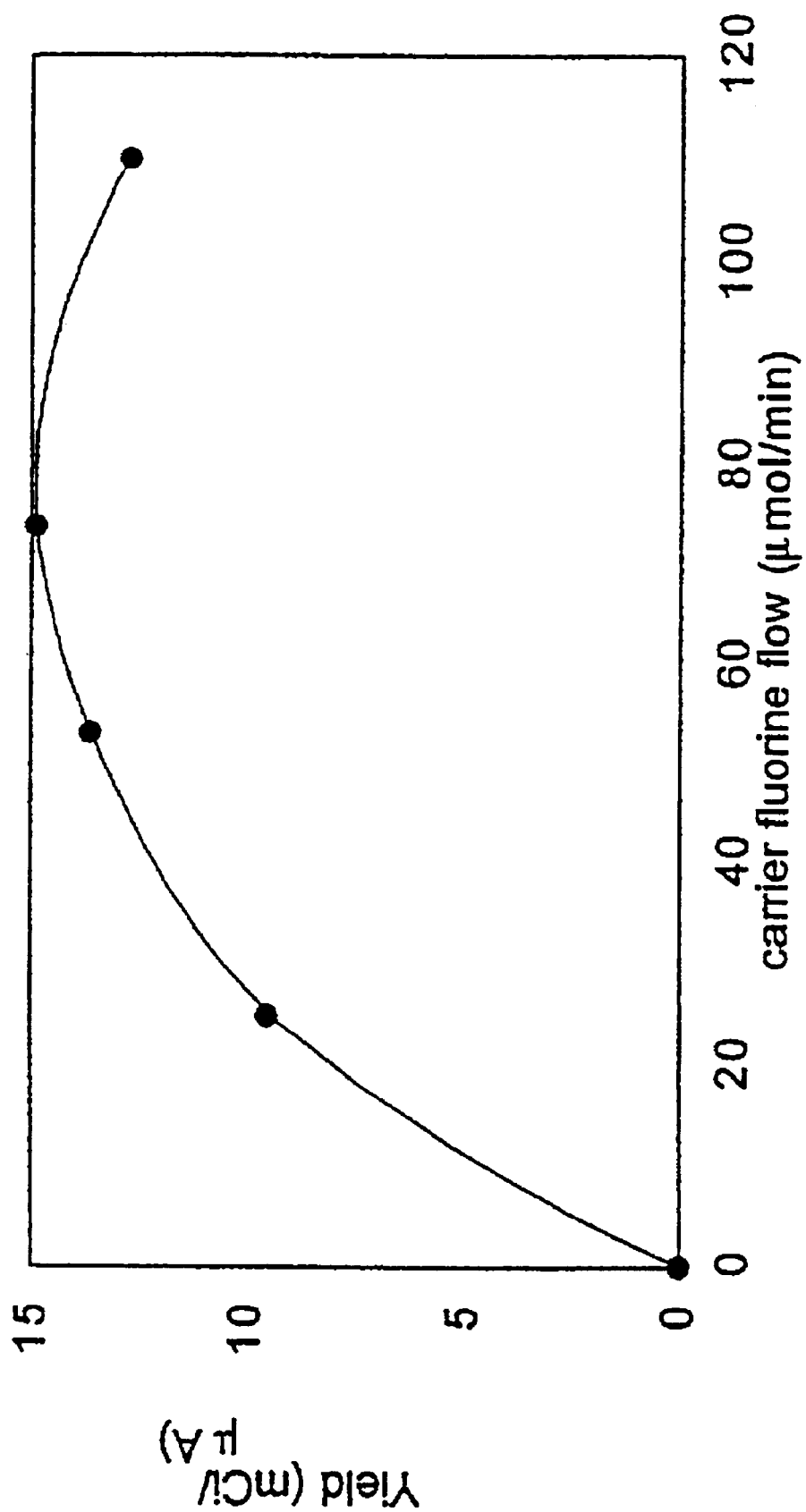
FIG. 6 is a graph showing the yield of $^{17}$F labeled $F_2$ as measured in mCi/μA versus the carrier $F_2$ flow rate in μmol/minute.

FIG. 6 is a graph of the yield of $^{17}$F labeled $F_2$ as measured in mCi/$\mu$A as a function of carrier $F_2$ flow as measured in $\mu$mol/minute at a fixed Ne pressure. As shown in the graph, a maximum yield of about 15 mCi/$\mu$A occurs at a $F_2$ flow of about 75 $\mu$mol/minute. The decrease in yield at higher concentrations of $F_2$ is attributed to dilution of the $^{20}$Ne due to the added helium in the helium/$F_2$ gas mixture.

The location of $^{17}$F labeled tracers such as $^{17}$F labeled fluoromethane and other $^{17}$F labeled fluoroalkanes can be determined using a simple method. Typically, the $^{17}$F labeled tracer is first generated using the processes of the present invention. The tracer is then administered to a test subject such as a human, animal, plant, process plant, or a chemical reaction. After the tracer has been administered to the test subject, the test subject is scanned using a radiosensitive detector. Examples of suitable radiosensitive detectors include, but are not limited to, scintillation detectors, Geiger counters, positron emission tomography scanners, single photon emission computed tomography scanners, and solid state detectors such as, but not limited to, PIN diodes, silicon-based detectors, and germanium-based detectors. A more preferred radiosensitive detector for use in the method of determining the location of an $^{17}$F labeled tracer is a positron emission tomography scanner or camera which may be used to perform positron emission tomography as described below as an example of a type of method of determining the location of an $^{17}$F labeled tracer.

Positron emission tomography can be readily accomplished using the $^{17}$F labeled fluoromethane and other $^{17}$F labeled fluoroalkanes produced by the process of the invention as tracers. Typically, the $^{17}$F labeled compound is administered to a test subject and then scans are collected on the test subject using a positron emission tomography scanner. $^{17}$F labeled fluoromethane or other $^{17}$F labeled fluoroalkanes are most preferably administered to human and animal test subjects by having the test subject inhale a gas mixture containing the $^{17}$F labeled material. Alternatively, the $^{17}$F labeled compound may be added to a saline solution and then administered to an animal or human test subject such as by intravenous injection. A condenser such as a Waters Sep-Pak Plus C18 cartridge filter may be used in conjunction with ethanol/dry ice to trap fluoroalkanes such as fluoromethane. The Waters Sep-Pak Plus C18 cartridge filter may then be rinsed with saline to produce the saline solution for administration.

Figure 7:
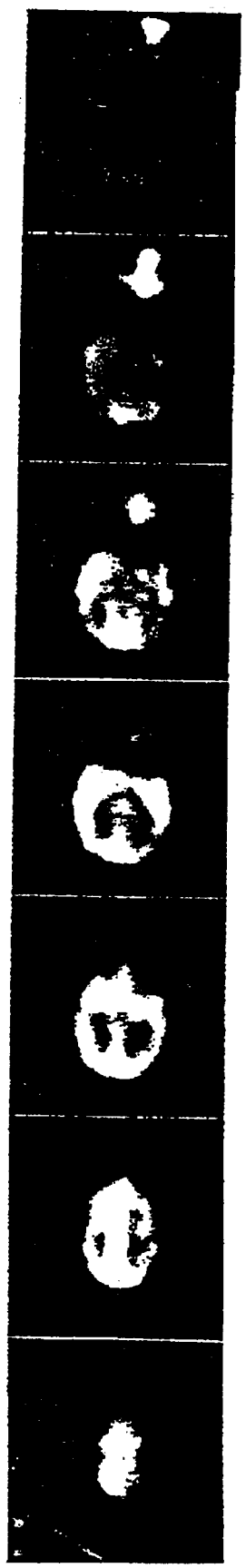
FIG. 7 is a series of brain flow images obtained from a test subject after steady state inhalation of 40 mCi of $^{17}$F labeled fluoromethane by the test subject. The test subject was a rhesus monkey and the instrument was an ECAT 944 PET scanner.

FIG. 7 shows brain flow images obtained with an ECAT 933 PET scanner using $^{17}$F labeled fluoromethane as a tracer. The test subject was a rhesus monkey. The $^{17}$F labeled fluoromethane was administered by having the rhesus monkey inhale the tracer at a steady state level of 40 mCi.

It is understood that the invention is not limited to the embodiments set forth herein for illustration, but embraces all such forms thereof as come within the scope of the following claims.

What is claimed is:

1. A method of generating a $^{17}$F labeled fluoroalkane, comprising:

contacting $^{17}$F labeled $F_2$ with an alkane, an unsubstituted alkene, a haloalkene, an unsubstitlited alkyne, or a haloalkyne in the presence of a metal oxide catalyst to produce the $^{17}$F labeled fluoroalkane.

2. The method of generating a $^{17}$F labeled fluoroalkane according to claim 1, wherein the $^{17}$F labeled $F_2$ is contacted with methane, the metal oxide catalyst is at a temperature above room temperature, and the $^{17}F$ labeled fluoroalkane is $^{17}F$ labeled fluoromethane.

3. The method of generating a $^{17}F$ labeled fluoroalkane according to claim 1, wherein the $^{17}F$ labeled $F_2$ is contacted with methane and $^{17}F$ labeled fluoromethane is produced.

4. The method of generating a $^{17}F$ labeled fluoroalkane according to claim 1, further comprising irradiating $^{20}Ne$ in a target gas stream comprising neon with protons to produce the $^{17}F$.

5. The method of generating a $^{17}F$ labeled fluoroalkane according to claim 4, wherein the neon in the target gas stream comprises natural neon gas.

6. The method of generating a $^{17}F$ labeled fluoroalkane according to claim 1, further comprising irradiating $^{16}O$ in a target gas stream comprising $O_2$ with deuterons to produce the $^{17}F$.

7. The method of generating a $^{17}F$ labeled fluoroalkane according to claim 1, wherein the $^{17}F$ labeled $F_2$ is contacted with the alkane, the unsubstituted alkene, the haloalkene, the unsubstituted alkyne, or the haloalkyne in the presence of the metal oxide catalyst and neon.

8. The method of generating a $^{17}F$ labeled fluoroalkane according to claim 1, wherein the metal oxide catalyst is silver oxide.

9. The method of generating a $^{17}F$ labeled fluoroalkane according to claim 8, wherein the $^{17}F$ labeled $F_2$ is contacted with methane, and the method further comprises maintaining the metal oxide catalyst at a temperature ranging from about 200° C. to about 600° C.

10. The method of generating a $^{17}F$ labeled fluoroalkane according to claim 9, wherein the metal oxide catalyst is maintained at a temperature ranging from about 400° C. to about 500° C.

11. The method of generating a $^{17}F$ labeled fluoroalkane according to claim 10, wherein the metal oxide catalyst is maintained at a temperature of about 450° C.

12. The method of generating a $^{17}F$ labeled fluoroalkane according to claim 8, wherein the $^{17}F$ labeled $F_2$ is contacted with the haloalkane or unsubstituted alkene or the haloalkane or unsubstituted alkyne, and the method further comprises maintaining the metal oxide catalyst at a temperature ranging from about 10° C. to about 600° C.

13. The method of generating a $^{17}F$ labeled fluoroalkane according to claim 12, wherein the metal oxide catalyst is maintained at a temperature ranging from about 20° C. to about 100° C.

14. The method of generating a $^{17}F$ labeled fluoroalkane according to claim 13, wherein the metal oxide catalyst is maintained at a temperature of about 25° C.

15. The method of generating a $^{17}F$ labeled fluoroalkane according to claim 1, wherein the $^{17}F$ labeled $F_2$ is contacted with the haloalkane or unsubstituted alkene or the haloalkane or unsubstituted alkyne.

16. The method of generating a $^{17}F$ labeled fluoroalkane according to claim 1, wherein the $^{17}F$ labeled $F_2$ is contacted with a haloalkene or a haloalkyne.

17. The method of generating a $^{17}F$ labeled fluoroalkane according to claim 16, wherein the haloalkene or the haloalkyne is a fluorinated alkene or alkyne.

18. The method of generating a $^{17}F$ labeled fluoroalkane according to claim 17, wherein the fluorinated alkene is a difluoroalkene.

19. The method of generating a $^{17}F$ labeled fluoroalkane according to claim 18, wherein the fluorinated alkene is 1,1-difluoroethylene and the $^{17}F$ labeled fluoroalkane is $^{17}F$ labeled 1,1,1,2-tetrafluoroethane.

20. The method of generating a $^{17}F$ labeled fluoroalkane according to claim 4, wherein the target gas stream comprises $F_2$ and neon comprising $^{20}Ne$.

21. The method of generating a $^{17}F$ labeled fluoroalkane according to claim 20, wherein the $^{20}Ne$ is irradiated with protons having an energy of greater than 8 MeV.

22. The method of generating a $^{17}F$ labeled fluoroalkane according to claim 21, wherein the $^{20}Ne$ is irradiated with protons having an energy of about 11 MeV.

23. The method of generating a $^{17}F$ labeled fluoroalkane according to claim 21, wherein the $^{20}Ne$ is irradiated with protons having an energy of about 16 MeV.

24. The method of generating a $^{17}F$ labeled fluoroalkane according to claim 21, further comprising producing the protons with a cyclotron.

25. The method of generating a $^{17}F$ labeled fluoroalkane according to claim 20, wherein the target gas stream further comprises helium.

26. The method of generating a $^{17}F$ labeled fluoroalkane according to claim 20, wherein the target gas stream comprises less than about 1.0 percent $F_2$.

27. The method of generating a $^{17}F$ labeled fluoroalkane according to claim 26, wherein the target gas stream comprises less than about 0.7 percent $F_2$.

28. The method of generating a $^{17}F$ labeled fluoroalkane according to claim 27, wherein the target gas stream comprises less than about 0.3 percent $F_2$.

29. The method of generating a $^{17}F$ labeled fluoroalkane according to claim 4, wherein the target gas stream is at a total pressure ranging from about 100 to about 400 psig.

30. The method of generating a $^{17}F$ labeled fluoroalkane according to claim 29, wherein the target gas is at a total pressure of from about 160 to about 240 psig.

31. The method of generating a $^{17}F$ labeled fluoroalkane according to claim 1, further comprising passing the $^{17}F$ labeled fluoroalkane through a scrubber.

32. The method of generating a $^{17}F$ labeled fluoroalkane according to claim 31, wherein the scrubber is a soda lime scrubber.

33. The method of generating a $^{17}F$ labeled fluoroalkane according to claim 4, wherein the $^{17}F$ is continuously generated by continuously irradiating the target gas stream with protons and the $^{17}F$ labeled fluoroalkcane is continuously produced by continuously contacting the $^{17}F$ labeled $F_2$ with the alkane, the unsubstituted alkane, the haloalkane, the unsubstituted alkane, or the haloalkyne.

34. The method of generating a $^{17}F$ labeled fluoroalkane according to claim 1, wherein the $^{17}F$ labeled $F_2$ is contacted with the alkane, and the alkane is a linear, branched chain, or cyclic alkane selected from the group consisting of ethane, propane, cyclopropane, butane, cyclobutane, methylcyclopropane, 2-methylpropane, 2-methylbutane, 2,3-dimethylbutane, methylcyclobutane, pentane, cyclopentane, hexane, methylcyclopentane, and cyclohexane.

* * * * *

UNITED STATES PATENT AND TRADEMARK OFFICE
CERTIFICATE OF CORRECTION

PATENT NO. : 6,585,953 B2  
DATED : July 1, 2003  
INVENTOR(S) : Andrew D. Roberts and Robert J. Nickles It is certified that error appears in the above-identified patent and that said Letters Patent is hereby corrected as shown below:

Column 10,
Line 62, please delete the word "unsubstitlited" and replace it with -- unsubstituted --.

Column 11,
Lines 39-40, please delete the first occurrence of the word "haloalkane" and replace it with -- haloalkene -- and delete the second occurrence of the word "haloalkane" and replace it with -- haloalkyne --.
Lines 52-53, please delete the first occurrence of the word "haloalkane" and replace it with -- haloalkene -- and delete the second occurrence of the word "haloalkane" and replace it with -- haloalkyne --.

Column 12,
Lines 50-51, please delete the words "the unsubstituted alkane, the haloalkane, the unsubstituted alkane" and replace them with the words -- the unsubstituted alkene, the haloalkane, the unsubstituted alkyne --.

Signed and Sealed this

Fourth Day of November, 2003

JAMES E. ROGAN  
*Director of the United States Patent and Trademark Office*

UNITED STATES PATENT AND TRADEMARK OFFICE
CERTIFICATE OF CORRECTION

PATENT NO.     : 6,585,953 B2                                     Page 1 of 1
DATED          : July 1, 2003
INVENTOR(S)    : Andrew D. Roberts and Robert J. Nickles It is certified that error appears in the above-identified patent and that said Letters Patent is hereby corrected as shown below:

Column 10,
Line 62, please delete the word "unsubstitlited" and replace it with -- unsubstituted --.

Column 11,
Lines 39-40, please delete the first occurrence of the word "haloalkane" and replace it with -- haloalkene -- and delete the second occurrence of the word "haloalkane" and replace it with -- haloalkyne --.
Lines 52-53, please delete the first occurrence of the word "haloalkane" and replace it with -- haloalkene -- and delete the second occurrence of the word "haloalkane" and replace it with -- haloalkyne --.

Column 12,
Lines 50-51, please delete the words "the unsubstituted alkane, the haloalkane, the unsubstituted alkane" and replace them with the words -- the unsubstituted alkene, the haloalkene, the unsubstituted alkyne --.

This certificate supersedes certificate of correction issued November 4, 2003.

Signed and Sealed this

Thirteenth Day of January, 2004

JON W. DUDAS
*Acting Director of the United States Patent and Trademark Office*